United States Patent [19]

Wojtowicz

[11] Patent Number: 4,871,486
[45] Date of Patent: Oct. 3, 1989

[54] PROCESS FOR MAKING METHYLPHOSPHONIC DICHLORIDE

[75] Inventor: John A. Wojtowicz, Cheshire, Conn.
[73] Assignee: Olin Corporation, Cheshire, Conn.
[21] Appl. No.: 680,629
[22] Filed: Dec. 12, 1984
[51] Int. Cl.[4] .............................................. C07F 9/42
[52] U.S. Cl. .................................................... 562/818
[58] Field of Search ..................................... 260/543 P

[56] References Cited

U.S. PATENT DOCUMENTS

| | | | |
|---|---|---|---|
| 2,847,469 | 8/1958 | Dawson et al. | 260/543 |
| 3,188,281 | 6/1965 | Briggeman et al. | 202/40 |
| 3,775,470 | 11/1973 | Vogel | 260/502.4 R |
| 3,950,413 | 4/1976 | Finke et al. | 260/543 P |
| 3,972,923 | 8/1976 | Finke et al. | 260/543 P |
| 4,213,922 | 7/1980 | Maier | 260/958 |
| 4,371,509 | 2/1983 | Grosse | 423/300 |
| 4,411,842 | 10/1983 | Hechenbleikner et al. | 260/543 |

OTHER PUBLICATIONS

Houben/Weyl, *Organische Phorphor Verbindungen*, vol. 12/1, (1963), pp. 386–390, Georg Thieme, Publ. (Stuttgart).
Chemicals Abstracts 92:42113u.
K. Moednitzer and R. E. Miller, "A Convenient One-Step, High Yield Preparation of Methylphosphonyl Dichloride From Dimethyl Memthylphosphonate", Syng. React. Inorg. Metal-Org. Chem. 4(5), pp. 417–427 (1974).

*Primary Examiner*—Paul J. Killos
*Attorney, Agent, or Firm*—William A. Simons

[57] ABSTRACT

Disclosed is a process for producing methylphosphonic dichloride comprising reacting dimethyl methylphosphonate with a chlorinating agent selected from the group consisting of thionyl chloride and phosgene in the presence of a catalytic amount of an inorganic halide selected from the group consisting of ammonium halide and metallic halides where the metal cation is selected from the metals of Groups IA, IIA, IIIB, IVB, VB, VIB, VIIB, VIIIB, IB, IIB and IIIA of the Periodic Table.

5 Claims, No Drawings

PROCESS FOR MAKING METHYLPHOSPHONIC DICHLORIDE

RIGHTS OF U.S. GOVERNMENT

The U.S. Government has rights in this invention pursuant to Contract No. DAAK11-84-C-0005 awarded by the Department of the Army.

BACKGROUND OF THE INVENTION

1. Field of the Invention

This invention relates to a process for making methylphosphonic dichloride by the chlorination of dimethyl methylphosphonate in the presence of selected catalytic agents.

2. Description of Prior Art

Methylphosphonic dichloride (also known as methyl dichlorophosphine oxide, methylphosphonyl dichloride or MPOD) is a well known chemical intermediate. For example, it may be converted into dimethyl pentaerythritol disphosphonate, which is useful as a flame-retardant. See U.S. Pat. No. 4,411,842 which issued to Hechenbleikner et al on Oct. 25, 1983. Further, MPOD may be converted into compounds having insecticidal activity. See U.S. Pat. No. 4,213,922, which issued to Maier on July 22, 1980.

Several synthetic routes for making MPOD have been suggested. See U.S. Pat. No. 4,411,842, noted above, for description of a number of different methods. One well known method is the uncatalyzed reaction of dimethyl methylphosphonate with thionyl chloride under reflux temperatures. See *React. Inorgan. Metal Org. Chem.*, 4, 417 (1974). The authors of this cited article report that MPOD may be obtained in a yield of 98% of theory. But, upon repeating their experiment, the patentee of U.S. Pat. No. 4,213,922 found that this product could only be obtained in yields from about 25 to 50% of theory. This finding is confirmed in the Comparison experiments set forth below. Moreover, this uncatalyzed method has the commercial disadvantage of being very slow. To improve the rate of reaction and yields, it was proposed in U.S. Pat. No. 4,213,922 that certain nitrogen-containing compounds, namely, selected N,N-disubstituted formamides, selected tertiary amines and selected N,N-disubstituted phosphoric acid triamides, be added to the reaction mixture in small catalytic-like amounts. But, these organic compounds or catalysts may be difficult to remove from the product.

Another catalytic method for preparing organophosphonyl dichlorides is discloses in U.S. Pat. No. 3,775,470 which issued to Vogel on Nov. 27, 1973. That patent teaches that organophosphonyl alkyl esters may be reacted with phosphorus pentachloride in the presence of a catalyst selected from a lithium halide or a mixture of a lithium halide and an alkali metal or alkaline earth metal halide. However, the reported yields of this catalyzed reaction are relatively low (i.e. 30–74% yields) and MPOD was not prepared. Thus, the production of highly pure MPOD at a reasonable cost remains a need.

BRIEF SUMMARY OF THE INVENTION

The present invention, therefore, is directed to a process for making methylphosphonic dichloride comprising:

reacting dimethyl methylphosphonate with a chlorinating agent selected from the group consisting of thionyl chloride and phosgene in the presence of a catalytic amount of an inorganic halide selected from the group consisting of ammonium halide and metallic halides where the metal cation is selected from the metals of Groups IA, IIA, IIIB, IVB, VB, VIB, VIIB, VIIIB, IB, IIB and IIIA of the Periodic Table.

DETAILED DESCRIPTION

It is believed that the primary reaction of the present invention occurs in two stages, namely the reaction of dimethyl methylphosphonate (DMMP) with one mole of thionyl chloride ($SOCl_2$) or phosgene ($COCl_2$) to form an intermediate monochloro compound $CH_3PO(OCH_3)Cl$; followed by the further reaction of this intermediate compound with another mole of $SOCl_2$ or $COCl_2$ to form the desired product. These reactions are illustrated by the following reaction equations (A) and (B) wherein $SOCl_2$ is the chlorinating agent:

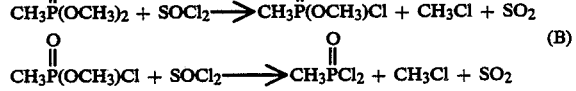

It should be noted that reactions (A) and (B) are not the only reactions that may occur. Polymer formation may also occur by the condensation of DMMP with MPOD. In the presence of excess MPOD, the resulting polymer will most likely have chloro end groups. In the presence of excess DMMP, the resulting polymer end groups will most likely be methoxy groups. These polymer formation reaction (which reduce the yield of the desired MPOD product) are illustrated by the following equations (C) and (D):

where n > m (Excess MPOD)

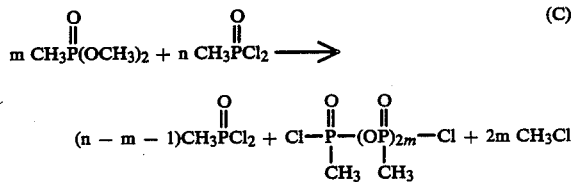

where m > n (Excess DMMP)

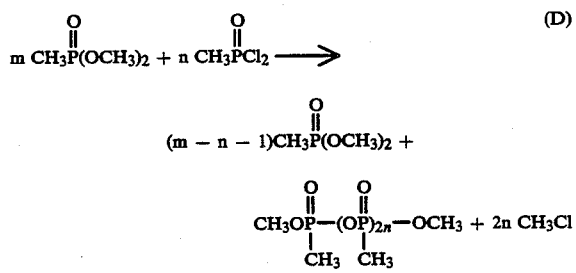

It is believed that the catalysts of the present invention do not prevent formation of these polymers, but instead allow their conversion back to the desired MPOD. This conversion is illustrated by following unzipping reaction (E):

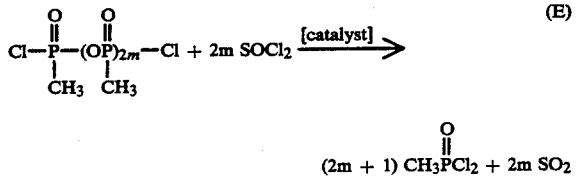

$$(2m + 1) \ CH_3\overset{\overset{O}{\|}}{P}Cl_2 + 2m \ SO_2$$

However, it should be recognized that the present invention is not intended to be limited to any particular theoretical reaction sequences for making MPOD.

As mentioned above, either $SOCl_2$ or $COCl_2$ may be utilized as a chlorinating agent for the present invention. The use of phosphorus-based chlorinating agents (e.g. $PCl_5$) as taught in U.S. Pat. No. 3,775,470, mentioned above, are unacceptable because they result in low MPOD product yields (e.g. about 70% of theory), even with a catalyst. Also, $PCl_5$ is relatively more expensive than either $SOCl_2$ or $COCl_2$ and, thus, economically disadvantageous. Furthermore, both $SOCl_2$ and $COCl_2$ are converted into easily separable volatile gases ($CH_3Cl$ and $SO_2$ or $CO_2$) whereas $PCl_5$ reacts with DMMP to form $POCl_3$ and highly flammable ethyl ether as by-products which must be removed from the reaction mixture by distillation. Furthermore, excess $PCl_5$ sublimes at a temperature close to the boiling point of DMMP, thereby contaminating the product. Thus, $PCl_5$ presents extreme processing difficulties on a commercial scale.

At least a stoichiometric amount of either of these two chlorinating agents is preferably employed. Recognizing that 2 moles of the chlorinating agent are needed to react stoichiometrically with 1 mole of DMMP to form 1 mole of MPOD, it is preferred to employ a mole ratio from about 2.0:1 to about 3.0:1 of either $SOCl_2$ or $COCl_2$ to DMMP. More preferably, this mole ratio is from about 2.05:1 to about 2.50:1.

As mentioned above, the catalysts for the reaction of the present invention may be inorganic halides selected from the group consisting of ammonium halides (e.g. $NH_4Cl$) and metal halides wherein the metal cation is selected from the group consisting of Group IA (e.g. Li, Na, K), IIA (e.g. Mg, Ca, Sr, Ba), IIIB (e.g. Y), IVB (e.g. Ti), VB (e.g. V), VIB (e.g. Cr), VIIB (e.g. Mn), VIIIB (e.g. Fe, Ni), IB (e.g. Cu), IIB (e.g. Cu), IIIA (e.g. Al) of the Periodic Table. These Groups correspond to the Groups shown on the Periodic Chart of the Elements printed on the front inside cover of The Merck Index—Tenth Edition (1983). The preferred catalysts are $NH_4Cl$, $NaCl$, $NaBr$, $NaI$, $KBr$, $CaCl_2$, $CaF_2$, $YCl_3$ $TiI_4$, $VI_2$, $MnCl_2$, $MnF_2$, $MnI_2$, $FeI_2$, and $NiBr_2$ because they have been shown to result in very high yields of MPOD within reasonable periods of time. It is believed that metal halide catalysts which are at least partially soluble in the reaction mixture (i.e. at least about 0.1 gram per liter of reaction mixture) are more effective catalysts. The most preferable catalysts found are $CaCl_2$ and $NaCl$ because of their cost and ease of handling. It should be noted that the term "metal halides" as used in the present specification and claims also refer to hydrated forms of these halides. Mixtures of the above-noted catalysts also may be employed. Furthermore, the present invention encompasses the in situ formation of these catalysts by the reaction of their corresponding metal oxides, hydroxides, bicarbonates or carbonates with an appropriate hydrogen halide.

Any amount of catalyst which is effective may be employed. Generally the concentration of catalyst employed will range from about 0.01% to about 10% by weight of DMMP originally employed. More preferably, this amount may range from about 0.5% to about 5.0% by weight of DMMP originally present.

The reaction of the present invention may be carried out in the presence of a solvent, but one is not necessary. A solvent may be used when the particular catalyst is not sufficiently soluble in the reactants. Ethers and other non-reactive polar organic solvents may be employed.

This reaction generally may be performed from moderate temperatures (e.g. about 50° C.) to the boiling point of DMMP (i.e. about 181° C.). More preferably, the reaction temperature of the present invention may range from about 75° C. to about 150° C. The most preferred reaction temperatures range from about 100° C. to about 130° C.

Pressure is not believed to have any significant effect on this reaction, but superatmospheric pressures up to about 100 atmospheres or subatmospheric pressures down to about 250 mm Hg may be employed. Atmospheric pressure is preferred because of cost and operating considerations.

A preferred procedure for conducting the reaction is to first charge the reaction vessel with DMMP and catalyst and heating this mixture to the desired reaction temperature. Then the $SOCl_2$ or $COCl_2$ is added beneath the surface of the DMMP to minimize their volatilization into the vent gas. The $SO_2$ (or $CO_2$) and $CH_3Cl$ by-product gases are vented from the reaction vessel and then scrubbed to remove any small amount of $SOCl_2$ or $COCl_2$ which might escape from the reactor. The chlorination of DMMP to MPOD is quite amenable to continuous operation. After the product is removed from the reaction vessel, it may be subjected to distillation, preferably under reduced pressure, to remove any remaining traces of $SOCl_2$ and leaving the catalyst as a residue. The distilled MPOD may be collected and stored until further use. It is possible to recycle the catalyst after this distillation, thus reducing raw material requirements. The absence of significant amounts of undesirable polymer by-products may allow for longer on-stream production times between equipment clean ups than the uncatalyzed reaction.

The present invention has several advantages over the prior art processes, MPOD may be produced by this process in essentially quantitative yields within a reasonable short reaction time. Also, the inorganic halide catalysts employed herein are non-volatile and, thus, do not contaminate the product as may occur in the case of the organic based catalysts disclosed in U.S. Pat. No. 4,213,922.

The following Examples and Comparison experiments further illustrate the present invention. All parts and percentages are by weight unless explicitly stated otherwise.

COMPARISONS 1-10 AND EXAMPLES 1-11

A series of experiments was carried out in a three neck, one liter glass flask fitted with an addition funnel, thermometer, condenser, nitrogen inlet, mechanical stirrer and a heating mantle. Dimethyl methylphosphonate and thionyl chloride were added to the flask using several different modes of addition, in some cases with a catalyst and in other cases without a catalyst. After addition, the reaction mixtures were heated for an additional time to drive the reaction to completion. Vent gases from the system which passed through the condenser were scrubbed in a methanolic ammonium hydroxide solution to prevent their escape into the atmosphere. Clean and dry glassware was employed in all experiments. After completion of heating, the cooled reaction mixture was transferred to a clean dry sample bottle and analyzed by NMR. The specific reaction conditions and product analyses are given in following Table 1. It is recognized that the yields of Examples 6 and 9 (with $ZnCl_2$ and $CuCl_2 \cdot 2H_2O$ as catalysts) are not much better than the Comparison experiments without catalysts. It is believed that these poor results may be due in part to inadequate solubility to the catalyst in the reaction mixture. It is also believed that these compounds would act as effective catalysts if they were used in larger concentrations or if a cosolvent was present.

and catalyst were added together to the flask and the mixture heated to reflux and maintained for specified times; see Table 2. Vent gases from this system which passed through the condenser were scrubbed in aa methanolic ammonium hydroxide solution to prevent their escape into the atmosphere. Oven dried glassware was used to each run. Upon termination of heating, the cooled reaction mixtures were transferred to dry $N_2$ flushed sample bottles and analyzed by NMR. The specific reaction conditions and product analyses are given in following Table 2. It is recognized that the yields of Examples 14, 19, 20, 31 and 34 (with $VCl_3$, $AlI_3$, $CrI_2$, $AlF_3$ and $YF_3$ as catalysts, respectfully) are not much better than the Comparisons in Table 1 which do not employ a catalyst. The poor results in some cases are believed due to inadequate solubility of the catalyst in the reaction mixture. It is also believed these compounds would be effective catalysts in larger concentra-

TABLE 1

| Comparison or Example | DMMP Moles | $SOCl_2$ Moles | Catalyst Type | Catalyst Amount (g.) | Addition of Reactants Mode | Addition of Reactants Time (h.) | Addition of Reactants Temperature (°C.) | Post Addition Reflux Time (h.) | Post Addition Reflux Temperature (°C.) |
|---|---|---|---|---|---|---|---|---|---|
| C-1 | 2.02 | 5.06 | None | — | a | 6.0 | 75–78 | 9.0 | 78–94 |
| C-2 | 1.09 | 2.73 | None | — | c | 0.0 | — | 1.0 | 71–92 |
| C-3 | 1.01 | 3.81 | None | — | a | 5.0 | 77–85 | 0.0 | — |
| C-4 | 1.09 | 2.73 | None | — | b | 13.0 | 110–130 | 0.0 | — |
| C-5 | 1.09 | 2.73 | None | — | a | 2.0 | 75–83 | 14.7 | 98 |
| C-6 | 1.01 | 2.52 | DMF | 75.0 | b | 3.3 | 95–109 | 0.3 | 108–140 |
| C-7 | 1.09 | 2.73 | DMF | 1.0 | a | 2.0 | 76–79 | 13.5 | 79–120 |
| C-8 | 1.09 | 2.73 | pyridine | 1.0 | b | 2.0 | 76–79 | 6.3 | 79–125 |
| C-9 | 1.10 | 2.73 | DMAC | 1.0 | a | 2.0 | 76–79 | 2.6 | 88–130 |
| C-10 | 1.09 | 2.73 | DMAC | 1.0 | b | 1.9 | 114–25 | 0.7 | 121–122 |
| E-1 | 1.09 | 2.73 | NaCl | 1.4 | a | 1.5 | 75–83 | 7.3 | 83–135 |
| E-2 | 1.09 | 2.73 | $CaCl_2$ | 1.4 | a | 2.0 | 74–80 | 0.5 | 80–150 |
| E-3 | 0.544 | 1.37 | KBr | 0.70 | a | 0.5–1.0 | 75 | 22 | 78–123 |
| E-4 | 0.544 | 1.37 | NaBr | 0.70 | a | 0.5–1.0 | 75 | 22 | 78–157 |
| E-5 | 0.544 | 1.37 | NaI | 0.70 | a | 0.5–1.0 | 75 | 18 | 83–163 |
| E-6 | 0.544 | 1.37 | $ZnCl_2$ | 1.00 | a | 0.5–1.0 | 75 | 22 | 81–88 |
| E-7 | 0.544 | 1.37 | $FeCl_3$ | 0.70 | a | 0.5–1.0 | 75 | 23 | 87–110 |
| E-8 | 0.544 | 1.37 | $AlCl_3$ | 0.70 | a | 0.5–1.0 | 75 | 3.6 | 74–132 |
| E-9 | 0.544 | 1.37 | $CuCl_2\ 2H_2O$ | 0.80 | a | 0.5–1.0 | 75 | 24 | 77–128 |
| E-10 | 0.544 | 1.40 | $MnCl_2\ 4H_2O$ | 1.1 | a | 0.5–1.0 | 75 | 4.3 | 75–130 |
| E-11 | 0.544 | 1.37 | $CrCl_3$ | 0.70 | a | 0.5–1.0 | 75 | 18.5 | 80–132 |

Mode: a = dropwise addition of DMMP to $SOCl_2$; b = dropwise addition of $SOCl_2$ to DMMP; c = DMMP and $SOCl_2$ were premixed and heated to reflux.

| Comparison or Example | Crude Product Grams | % MPOD Yield[d] |
|---|---|---|
| C-1 | N.M. | 39 |
| C-2 | N.M. | 8 |
| C-3 | 377 | 0 |
| C-4 | 144 | 28 |
| C-5 | 177 | 59 |
| C-6 | 224 | 66 |
| C-7 | 169 | 97 |
| C-8 | 169 | 100 |
| C-9 | 167 | 99 |
| C-10 | 187 | 100 |
| E-1 | 162 | 100 |
| E-2 | 148 | 93 |
| E-3 | 76.5 | 99.5 |
| E-4 | 72.9 | 99.5 |
| E-5 | 72.2 | 93 |
| E-6 | 98.2 | 35 |
| E-7 | 80.6 | 73 |
| E-8 | 73.4 | 87 |
| E-9 | 75.8 | 55 |
| E-10 | 76.4 | 92 |
| E-11 | 77.9 | 83 |

N.M. = Not Measured
d = Analytical yield based on $^{31}P$ nmr analysis, balance of yield is polymer. Conversion of DMMP was 100% in all runs

EXAMPLES 13–34

A series of experiments were carried out in a $N_2$ flask 250-ml erlenmeyer flask fitted with a condenser, heated on a hot plate and vented to a scrubber. DMMP, $SOCl_2$, tions or if a cosolvent was present.

TABLE 2

| Comparison or Example | DMMP Moles | SOCl₂ Moles | Catalyst Type | Catalyst Amount (g.) | Reaction Time (h.) |
|---|---|---|---|---|---|
| E-12 | 0.544 | 1.37 | $CaF_2$ | 0.70 | 20 |
| E-13 | 0.544 | 1.37 | $TiCl_4$ | 0.70 | 21.5 |
| E-14 | 0.544 | 1.37 | $VCl_3$ | 0.70 | 21.5 |
| E-15 | 0.544 | 1.41 | $YCl_3 \cdot 6H_2O$ | 1.09 | 21.5 |
| E-16 | 0.544 | 1.37 | $NH_4Cl$ | 0.70 | 22 |
| E-17 | 0.544 | 1.37 | $FeI_2$ | 0.70 | 24 |
| E-18 | 0.544 | 1.37 | $ZnI_2$ | 0.70 | 24 |
| E-19 | 0.544 | 1.37 | $AlI_3$ | 0.70 | 24 |
| E-20 | 0.544 | 1.37 | $CrI_3$ | 0.70 | 24 |
| E-21 | 0.544 | 1.37 | $TiI_4$ | 0.70 | 24 |
| E-22 | 0.544 | 1.37 | $ZrCl_4$ | 0.70 | 24 |
| E-23 | 0.544 | 1.37 | $CuBr_2$ | 0.70 | 24 |
| E-24 | 0.544 | 1.37 | $NiBr_2$ | 0.70 | 24 |
| E-25 | 0.544 | 1.37 | $MnI_2$ | 0.70 | 24 |
| E-26 | 0.544 | 1.37 | $VI_2$ | 0.70 | 24 |
| E-27 | 0.544 | 1.37 | $CrF_3$ | 0.70 | 24 |
| E-28 | 0.544 | 1.37 | $CuF_2$ | 0.70 | 24 |
| E-29 | 0.544 | 1.37 | $CuI_2$ | 0.70 | 24 |
| E-30 | 0.544 | 1.37 | $HgBr_2$ | 0.70 | 24 |
| E-31 | 0.544 | 1.37 | $AlF_3$ | 0.70 | 24 |
| E-32 | 0.544 | 1.37 | $MnF_2$ | 0.70 | 24 |
| E-33 | 0.544 | 1.37 | $NiF_2$ | 0.70 | 24 |
| E-34 | 0.544 | 1.37 | $YF_3$ | 0.70 | 24 |

| Comparison or Example | Crude Product Grams | % MPOD Yield[a] |
|---|---|---|
| E-12 | 76.5 | 97 |
| E-13 | 79.6 | 78 |
| E-14 | 83.8 | 64 |
| E-15 | 74.7 | 94 |
| E-16 | 75.6 | 94 |
| E-17 | 83.0 | 93 |
| E-18 | 89.1 | 71 |
| E-19 | 65.1 | 52 |
| E-20 | 90.0 | 65 |
| E-21 | 72.9 | 92 |
| E-22 | 87.6 | 79 |
| E-23 | 68.6 | 78 |
| E-24 | 80.1 | 91 |
| E-25 | 76.4 | 92 |
| E-26 | 74.0 | 95 |
| E-27 | 81.1 | 84 |
| E-28 | 71.4 | 84 |
| E-29 | 72.8 | 75 |
| E-30 | 96.2 | 71 |
| E-31 | 67.7 | 52 |
| E-32 | 76.3 | 95 |
| E-33 | 68.9 | 88 |
| E-34 | 87.8 | 41 |

[a] = Analytical yield based on 31p nmr analysis, balance of yield is polymer. Conversion of DMMP was 100% in all runs.

What is claimed is:

1. A process for producing methylphosphonodichloride comprising:
reacting dimethyl methylphosphonate with a chlorinating agent selected from the group consisting of thionyl chloride and phosgene at a temperature from about 50° C. to about 181° C. in the presence of a catalytic amount of an inorganic halide selected from the group consisting of $NH_4Cl$, $NaCl$, $NaBr$, $NaI$, $KBr$, $CaF_2$, $CaCl_2$, $MnF_2$, $MnCl_2$, $MnI_2$, $TiI_4$, $NiBr_2$, $FeI_2$, $YCl_3$ and $VI_2$.

2. The process of claim 1 wherein said catalyst is $CaCl_2$.

3. The process of claim 1 wherein said catalyst is NaCl.

4. The process of claim 1 wherein an inert solvent is added to the reaction mixture.

5. The process of claim 1 wherein said catalyst is formed in situ in the reaction mixture.

* * * * *